United States Patent [19]

Kikuchi

[11] Patent Number: 4,988,304
[45] Date of Patent: Jan. 29, 1991

[54] ELECTRODE DEVICE INCLUDING HIGH VOLTAGE SLIP-RING ELECTRODES

[75] Inventor: Kouki Kikuchi, Tochigi, Japan

[73] Assignee: Kabushiki Kaisha Toshiba, Kawasaki, Japan

[21] Appl. No.: 389,800

[22] Filed: Aug. 4, 1989

[30] Foreign Application Priority Data

Aug. 10, 1988 [JP] Japan .................................. 63-198012

[51] Int. Cl.⁵ ....................... H01R 39/10; A61B 6/03; H01B 17/14
[52] U.S. Cl. ...................................... 439/13; 174/177; 378/15
[58] Field of Search .................... 174/138 R, 171, 176, 174/177, 178; 378/4, 11, 13, 15, 17, 201, 202; 439/13-30; 310/143, 147, 232

[56] References Cited

U.S. PATENT DOCUMENTS

| 2,246,904 | 6/1941 | Stockinger | 174/171 |
| 4,329,004 | 5/1982 | Lewis | 378/15 X |
| 4,644,573 | 2/1987 | Palermo et al. | 378/15 |

FOREIGN PATENT DOCUMENTS 535042 10/1955 Italy .................................. 174/177

*Primary Examiner*—Laramie E. Askin
*Attorney, Agent, or Firm*—Oblon, Spivak, McClelland, Maier & Neustadt

[57] ABSTRACT

An electrode device including an insulating body, at least one conductor mounted on the insulating body, and an insulating member mounted on the conductor and supporting high voltage slip-ring electrodes to which high voltages are applied.

5 Claims, 2 Drawing Sheets

ELECTRODE DEVICE INCLUDING HIGH VOLTAGE SLIP-RING ELECTRODES

BACKGROUND OF THE INVENTION

1. Field of the Invention

The present invention relates to an electrode device which includes high voltage slip-ring electrodes.

2. Description of the Background Art

There is shown in FIG. 1 a conventional electrode device including a high voltage slip-ring electrode.

In FIG. 1, the device 1 includes a high voltage slip-ring electrode 6, an insulating body 3, and first and second conductors 2 and 4 partially buried to their half portions in the top and bottom portions of the insulating body 3 having an approximately spherical form. The second conductor 4 is mounted on a base member 5. The electrode 6 is mounted on the top of the first conductor 2, and a high voltage is applied from an exterior power supply to the electrode 6.

In the conventional electrode device 1, only one electrode 6 can be supported by the parts 2 and 3. For instance, even when high voltages having an about several tens of voltage difference from one another are supplied to plural electrodes and such electrodes are supported in the conventional manner, each electrode requires one conductor 2 and insulating body 3, which is disadvantageous and very much uneconomical.

SUMMARY OF THE INVENTION

Accordingly, it is an object of the present invention to provide an electrode device free from the aforementioned disadvantages and defects of the prior art which is capable of reducing the number of electrode devices needed in any installation, and which is simple in construction.

In accordance with one aspect of the present invention, there is provided an electrode device including high voltage slip-ring electrodes, an insulating body, at least one conductor mounted on the insulating body, and an insulating member mounted on the conductor and supporting the high voltage slip-ring electrodes to which high voltages are applied.

BRIEF DESCRIPTION OF THE DRAWINGS

The above and other objects, features and advantages of the present invention will more fully appear from the following description of the preferred embodiment with reference to the accompanying drawings, in which.

DESCRIPTION OF THE PREFERRED EMBODIMENT

Figure 2:
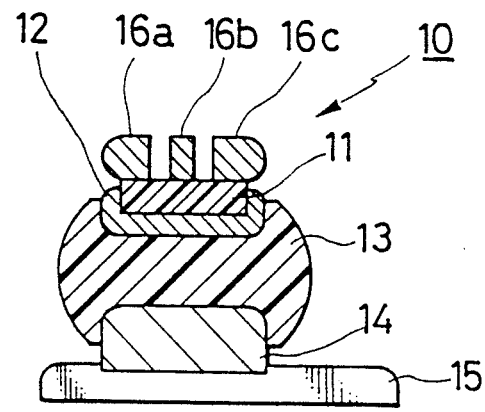
FIG. 2 is a longitudinal cross section of an electrode device according to the present invention.

Referring now to the drawings, wherein like reference characters designate like or corresponding members throughout the several views, there is shown in FIG. 2 one embodiment of an electrode device according to the present invention.

As shown in FIG. 2, the electrode device 10 comprises an insulating body 13 having an approximately spherical form, first and second conductors 12 and 14 partially buried in the top and bottom portions of the insulating body 13, respectively, an insulating member 11, and a plurality of high voltage slip-ring electrodes 16a, 16b and 16c, the insulating member 11 being partially buried in the upper portion of the first conductor 12. The high voltage slip-ring electrodes 16a, 16b and 16c are insulated or isolated from one another by the insulating member 11. The second conductor 14 is mounted on a base frame 15.

In this embodiment, high voltages such as 40 to 70 kV are applied to the high voltage electrodes 16a, 16b and 16c, and, when the voltage differences among the high voltages to be applied to the electrodes 16a, 16b and 16c are low such as 5 to 20 volts, it is not always necessary to ensure the high voltage insulation among the electrodes, and hence the insulation of the insulating member 11 may not be broken by such voltage differences. Hence, in this case, the three high voltage electrodes 16a, 16b and 16c can be supported at the same time by using the construction shown in FIG. 2 without causing any trouble.

Figure 3:
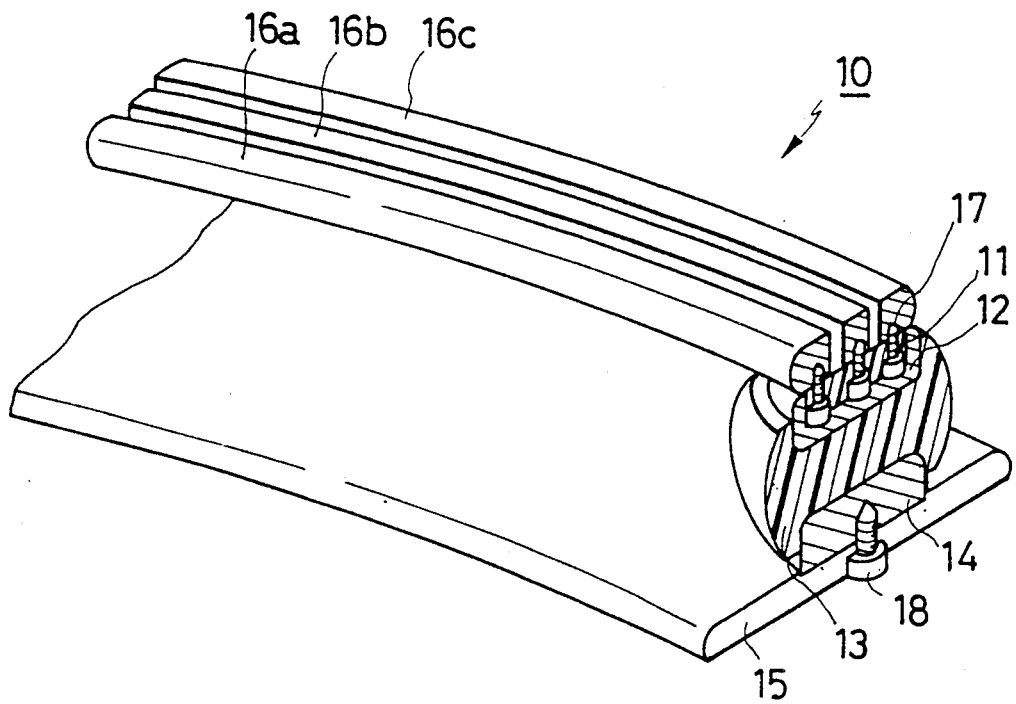
FIG. 3 is a fragmentary perspective view, partly in section, of the electrode device shown in FIG. 2 for use in an X-ray CT scanner.

In FIG. 3, there is shown the above-described electrode device 10 applied to an X-ray CT (computed tomography) scanner.

In an X-ray CT scanner, a combination of an X-ray tube and an X-ray sensor or receiver are arranged on opposite sides of an object such as a subject positioned therebetween so that the X-ray tube, the object and the X-ray receiver are aligned along one line. The X-ray tube emits X-rays to the X-ray receiver through the object, and the combination of the X-ray tube and X-ray receiver is simultaneously rotated around the object at the same angular speed in the same direction in order to obtain X-ray photography data by irradiating the X-rays to the object from the various different directions.

In such an X-ray CT scanner, the X-ray tube and the X-ray receiver are mounted on a rotary ring frame in its opposite sides with respect to the axis thereof, and electric power is supplied to the X-ray tube through a slip ring device. The slip ring device comprises slip-ring electrodes to be mounted to a fixed ring frame and brush electrodes mounted to the rotary ring frame, and the brush electrodes slidably contact the slip-ring electrodes while the X-ray tube and the X-ray receiver together with the rotary ring frame are rotated around the object. These slip-ring electrodes are parts of the electrode device according to the present invention.

In FIG. 3, the electrodes 16a, 16b and 16c act as the slip-ring electrodes slidably contacting the brush electrodes (not shown), and the base frame 15 constitutes a fixed ring frame. The three electrodes 16a, 16b and 16c are mounted to the insulating member 11 by bolts 17 from the insulating member side, and the electrode device 10 is secured to the base frame 15 by mounting the second conductor 14 to the base frame 15 from the base frame side.

Figure 4:
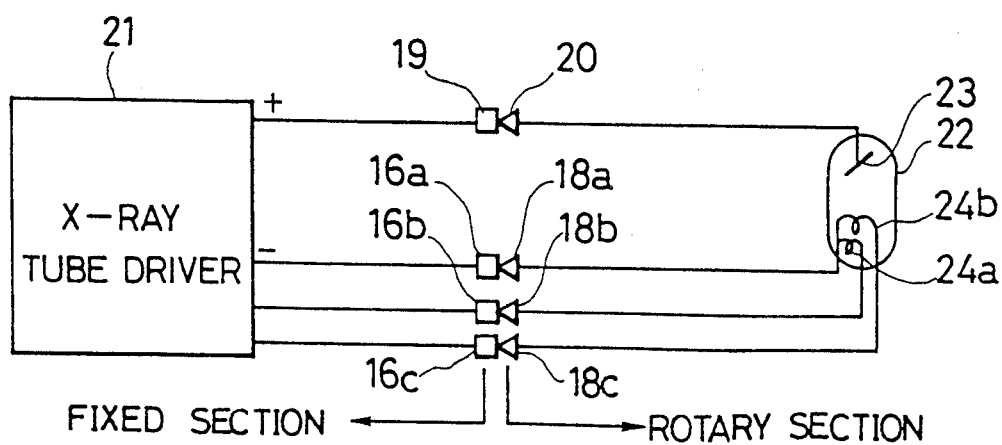
FIG. 4 is a circuit diagram including the electrode device shown in FIG. 2 for use in the X-ray CT scanner.

In FIG. 4, there is schematically shown a connection circuit of an X-ray tube 22 having an anode 23 and first and second filaments 24a and 24b therein, an X-ray tube driver 21 for supplying electric power to the X-ray tube 22, slip-ring electrodes 16a, 16b, 16c and 19 forming parts of electrode devices, and brush electrodes 18a, 18b, 18c and 20 slidably contacting the slip-ring electrodes 16a, 16b, 16c and 19 for use in an X-ray CT scanner. In this embodiment, the X-ray tube driver 21 and the slip-ring electrodes 16a, 16b, 16c and 19 are mounted to a fixed ring frame, and the X-ray tube 22 and the brush electrodes 18a, 18b, 18c and 20 are mounted to a rotary ring frame.

Figure 1:
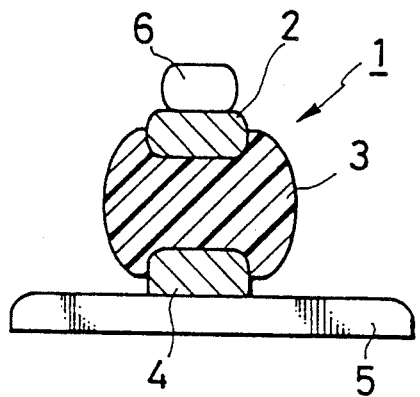
FIG. 1 is a longitudinal cross section of a conventional electrode device.

In this embodiment, the slip-ring electrodes 16a, 16b and 16c are parts of the electrode device 10 according to the present invention, as shown in FIG. 3, and the ring electrode 19 is part of the conventional electrode device 1 shown in FIG. 1. In the X-ray tube 22, one of the first and second filaments 24a and 24b is selectively used for a large or small focusing point. The heating voltage of the first and second filaments 24a and 24b is several to several tens of volts. In this case, for instance, a high voltage of approximately 75 kV is applied between the anode 23 and the first or second filament 24a or 24b. Hence, high voltages are applied to the slip-ring electrodes 16a, 16b and 16c used as negative electrodes. However, the differences among the high voltages applied to the slip-ring electrodes 16a, 16b and 16c are approximately at most several volts, and thus the insulating member 11 of the electrode device 10 may not be broken due to the voltage differences.

As described above, the electrode device of the present invention can effectively include high voltage slip-ring electrodes as negative electrodes of a slip-ring device for use in an X-ray CT scanner. Of course, the electrode device of the present invention can be used for other devices or apparatuses in addition to an X-ray CT scanner. It is readily understood that the number of electrode devices can be largely reduced according to the present invention when a plurality of electrodes to which high voltages are applied are supported by a single insulating member.

Although the present invention has been described in its preferred embodiment with reference to the accompanying drawings, it is readily understood that the present invention is not restricted to the above-described preferred embodiment, and various changes and modifications may be made in the present invention by those skilled in the art without departing from the spirit and scope of the present invention.

What is claimed is:

1. An electrode device for applying electric power to an electrical apparatus mounted on a rotary frame, comprising:
   an insulating body;
   first and second conductors provided on substantial portions, respectively, of a top and a bottom of the insulating body;
   a insulating member mounted on said first conductor; and
   plural high voltage slip-ring electrodes mounted on said insulating member and adapted to make sliding electrical connection to a plurality of slip-ring brush electrodes mounted on said rotary frame during rotating movement of said rotary frame.

2. The electrode device of claim 1, wherein said first and second conductors are partially buried in the top and bottom of the insulating body, and the insulating member is partially buried in the first conductor.

3. The electrode device of claim 1, wherein the insulating member is partially buried in the first conductor.

4. The electrode device of claim 1, wherein the slip-ring electrodes are isolated from one another by the insulating member.

5. The electrode device of claim 1, wherein the insulating body has an approximately spherical form.

* * * * *